United States Patent [19]
Allen et al.

[11] Patent Number: 5,780,516
[45] Date of Patent: Jul. 14, 1998

[54] MATERIAL AND METHODS FOR INHIBITING BACTERIAL CELL WALL BIOSYNTHESIS

[75] Inventors: Charles M. Allen; Harry S. Nick, both of Gainesville, Fla.

[73] Assignee: University of Florida, Gainesville, Fla.

[21] Appl. No.: 827,521

[22] Filed: Mar. 28, 1997

[51] Int. Cl.⁶ ............................................. A61K 31/075
[52] U.S. Cl. ............................................. 514/715
[58] Field of Search ................................. 514/715

[56] References Cited

U.S. PATENT DOCUMENTS 3,665,040   5/1972   Ruegg et al. ..................... 260/614 R

OTHER PUBLICATIONS

Cain, Brian D., Peter J. Norton, Willis Eubanks, Harry S. Nick, Charles M. Allen (1993) "Amplification of the bacA Gene Confers Bacitracin Resistance to *Escherichia coli*" Journal of Bacteriology 175:123784–3789.

*Primary Examiner*—Kevin E. Weddington
*Attorney, Agent, or Firm*—Saliwanchik, Lloyd & Saliwanchik

[57] ABSTRACT

The subject invention pertains to materials and methods for inhibiting bacterial growth. Specifically provided are compounds which control bacteria by interfering with cell wall synthesis.

10 Claims, 5 Drawing Sheets

MATERIAL AND METHODS FOR INHIBITING BACTERIAL CELL WALL BIOSYNTHESIS

BACKGROUND OF THE INVENTION

Despite the existence of many useful antibiotics, bacterial infections remain a major problem affecting human and animal health, agriculture, and industrial processes. The continued emergence of resistant bacteria heightens the need for the identification of new and effective antibacterial agents. The most advantageous of the antibacterial agents are those which can be used to selectively control bacteria without posing any health hazards for humans or animals. The identification of such agents is fraught with difficulties and uncertainties due in part to the many biochemical similarities between all living organisms. The identification of antibacterial agents remains an empirical process requiring extensive effort and the investment of substantial resources.

Bacteria in general synthesize a variety of extracellular glycans which provide structural integrity and a protective "wall" to the cell. Inhibition of the biosynthesis of this "wall" has been a favored approach in the design of drugs for the treatment of infectious disease because animal cells do not synthesize these walls. Most of the widely used and clinically effective antibiotics, such as the penicillins (cephalosporins) and vancomycin, function because they inhibit bacterial cell wall biosynthesis. The metabolic targets of each of these drugs are enzymes involved in the polymerization of the glycan chain and the cross-linking of the glycan chains. The biochemical pathway involved in cell wall synthesis is shown in FIG. 1.

One component of importance in cell wall biosynthesis is a $C_{55}$ isoprenoid lipid called undecaprenyl phosphate ($C_{55}$-P). This lipid acts as a catalyst in gathering and transferring carbohydrate residues to the growing cell wall. The synthesis of a repeating saccharide unit of peptidoglycan occurs on the $C_{55}$ isoprenoid lipid at the cytoplasmic face to the inner plasma membrane. This saccharide unit, while linked to the lipid, is translocated to the paraplasmic surface of the membrane where these sugars are transferred to the growing peptidoglycan.

The translocation of the $C_{55}$ isoprenoid lipid back to the cytosolic compartment may be an energy dependant process. In an alternate pathway, the $C_{55}$ isoprenoid lipid is hydrolyzed to free undecaprenol ($C_{55}$OH), which is translocated in an energy independent or low energy process to the cytosolic side of the membrane. At the cytosolic membrane surface, undecaprenol is then phosphorylated by a ATP-dependant undecaprenol kinase to regenerate the lipid, undecaprenyl phosphate, necessary for the next saccharide translocation process. The undecaprenol kinase enzyme is encoded by the gene known as bac-A which has been described by Cain et al. [Cain, Brian D., Peter J. Norton, Willis Eubanks, Harry S. Nick, Charles M. Allen (1993) "Amplification of the bacA Gene Confers Bacitracin Resistance to *Escherichia coli*" *J.Bacteriology* 175(12):3784–3789].

Although de novo biosynthesis provides the bulk of the initial pool of undecaprenyl phosphate, two alternative mechanisms are involved in maintaining an adequate pool size of C55-P for cell growth: 1) regeneration of undecaprenyl phosphate from the hydrolysis of undecaprenyl phosphate following saccharide transfer to the growing glycan; and 2) phosphorylation of free undecaprenol. The phosphorylation of free undecaprenol has previously been described as a "salvage" pathway. Although the enzyme responsible for the phosphorylation of free undecaprenol was crystallized over 20 years ago, there is no information published about its mechanism of action and little is known about its metabolic function.

BRIEF SUMMARY OF THE INVENTION

The subject invention pertains to materials and methods for killing bacteria and/or inhibiting their growth. More specifically, the subject invention concerns materials and methods which can be used to disrupt the processes by which the bacterial cell wall is established and maintained. In a specific embodiment of the subject invention, bacterial growth is inhibited by the application of a compound which interferes with a pathway critical for cell wall biosynthesis. Specifically, the subject invention provides compounds which interfere with the bacterial cell's ability to maintain sufficient amounts of the $C_{55}$ isoprenoid lipid known as undecaprenyl phosphate ($C_{55}$-P).

In a particularly preferred embodiment, the compounds useful according to the subject invention interfere with the bacterial cell's ability to regenerate $C_{55}$-P after the $C_{55}$-P has participated in the transportation of a saccharide unit (XY) across the plasma membrane from the cytosol to the periplasmic space. In accordance with the subject invention it has been determined that the regeneration of $C_{55}$-P proceeds, at least in part, through the initial hydrolysis of periplasmic $C_{55}$-P to $C_{55}$OH followed by transport of the $C_{55}$OH across the plasma membrane into the cytosol. The cytosolic $C_{55}$OH is then converted to $C_{55}$-P through the action of a phosphorylating kinase known as the undecaprenol kinase enzyme. The subject invention involves the disruption of the conversion of $C_{55}$OH to $C_{55}$-P. The disruption of this step in the cell wall biosynthetic pathway has been found to advantageously result in the inhibition of bacterial growth.

In a specific embodiment, the subject invention provides substrate mimics which can be, for example, lipid ethers which compete with $C_{55}$OH for the undecaprenol kinase enzyme thereby reducing the rate of conversion of $C_{55}$OH to $C_{55}$-P. Typically, the substrate mimics of the subject invention would not have a terminal hydroxyl group. Instead, an ether group or other group which cannot be enzymatically converted by the kinase is present on the substrate mimic. In a preferred embodiment, the ether is a methyl or ethyl ether, but other ethers could also be used. By disrupting the normal metabolism of $C_{55}$-P according to the subject invention it is possible to achieve a cessation or significant inhibition of cell wall synthesis. Consequently, bacterial growth is inhibited.

The bacteria inhibitor compounds of the present invention can be used for the preparation of pharmaceutical compositions which contain an effective amount of the active compounds, preferably in admixture with a significant amount of inorganic or organic, solid or liquid pharmaceutically acceptable excipients. The invention also relates to such pharmaceutical compositions and to the preparation and use thereof.

The pharmaceutical compositions of this invention are suitable for parenteral, e.g. intravenous or intramuscular, administration, and, as circumstances may require, also for oral administration or topical application.

DETAILED DISCLOSURE OF THE INVENTION

Figure 1:
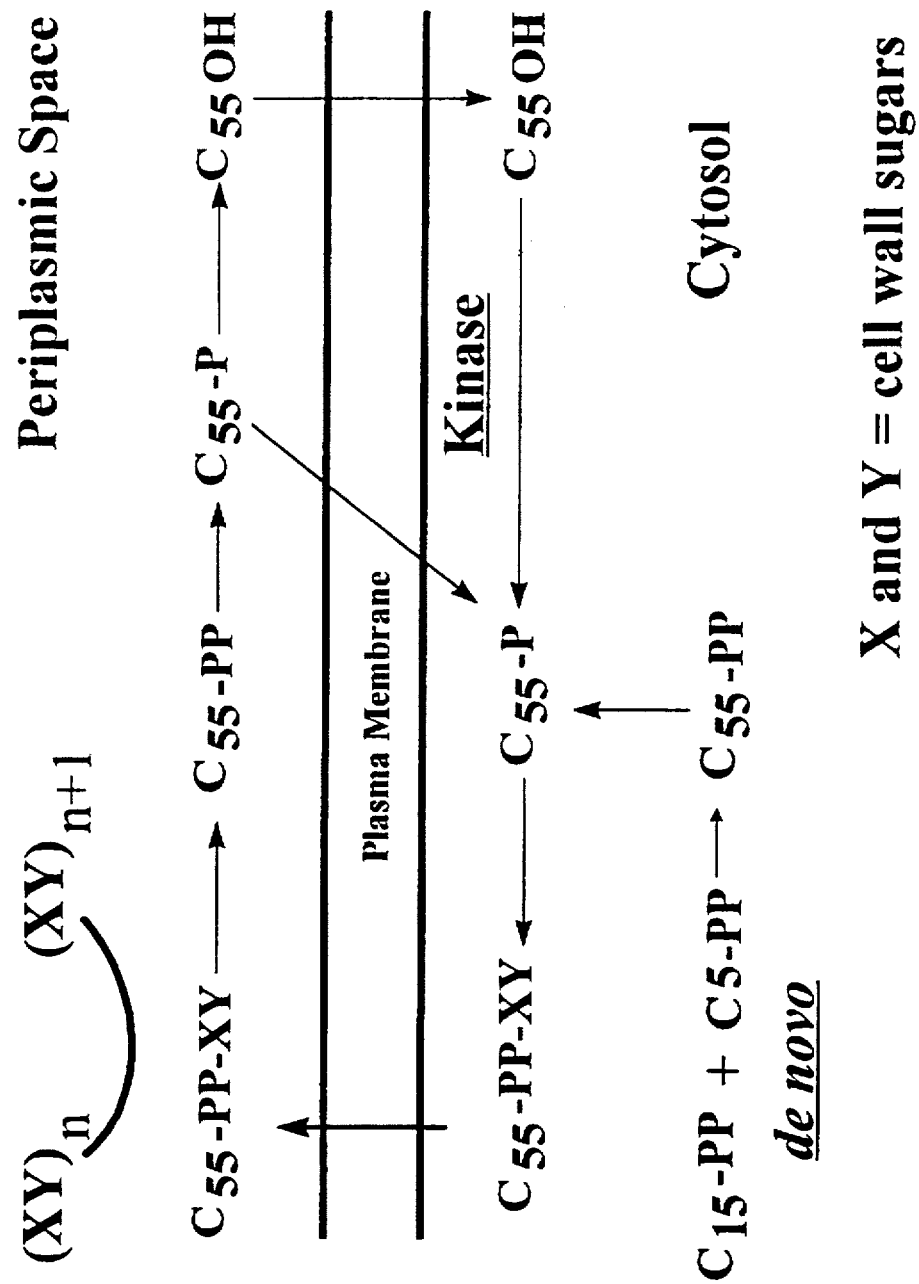
FIG. 1 shows the metabolic pathway involved in bacterial cell wall biosynthesis. In a preferred embodiment, the compounds of the subject invention disrupt the kinase-mediated conversion of $C_{55}$OH to $C_{55}$-P. The disruption of this conversion reduces the amount of $C_{55}$-P available for transporting saccharides (XY) across the plasma membrane into the periplasmic space.
Figure 2:
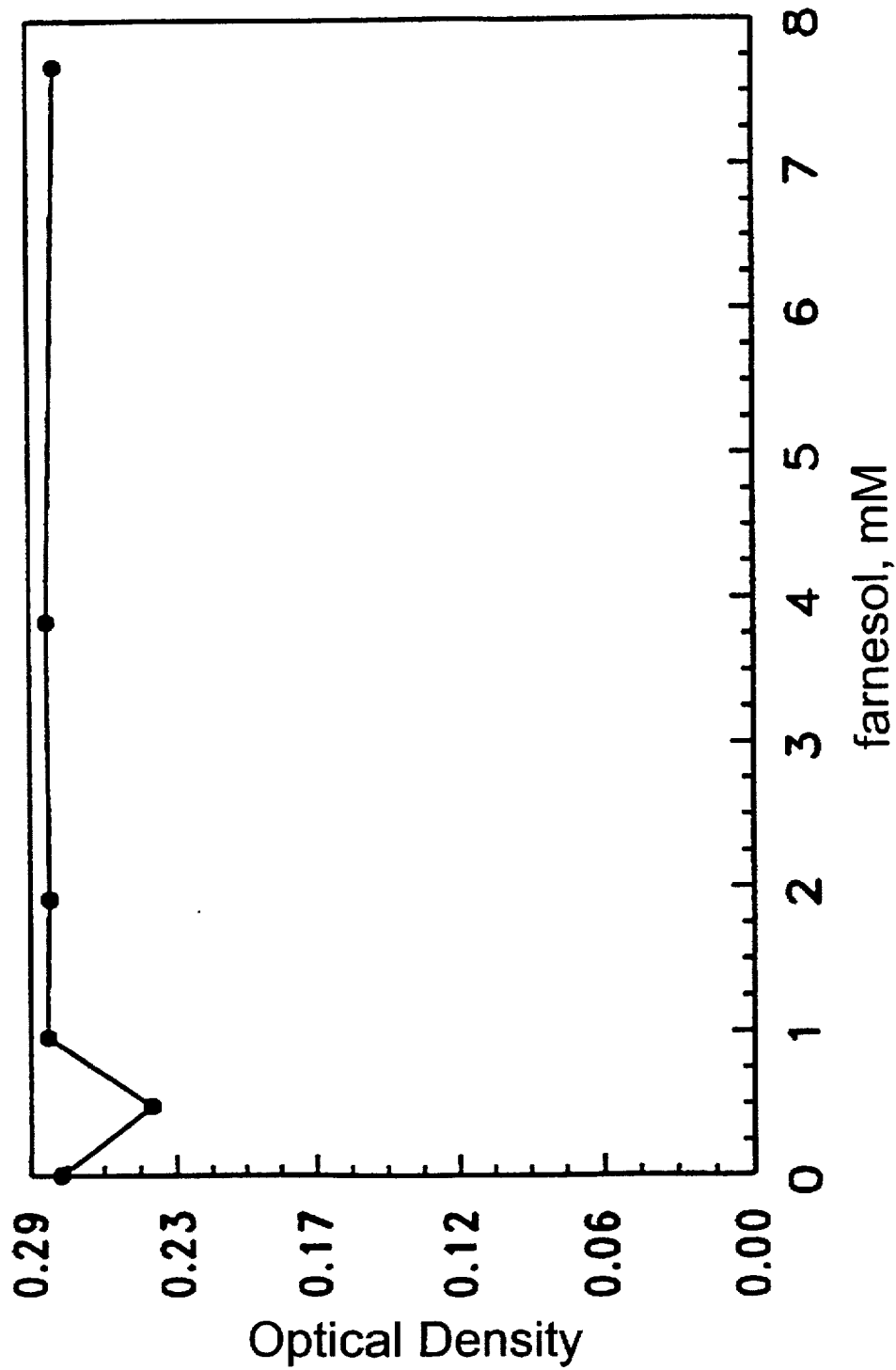
FIG. 2 shows the inhibition of bacterial growth resulting from the administration to *E. coli* of farnesol which is a $C_{15}$ alcohol with three double bonds. The figure shows little inhibition of bacterial growth.
Figure 3:
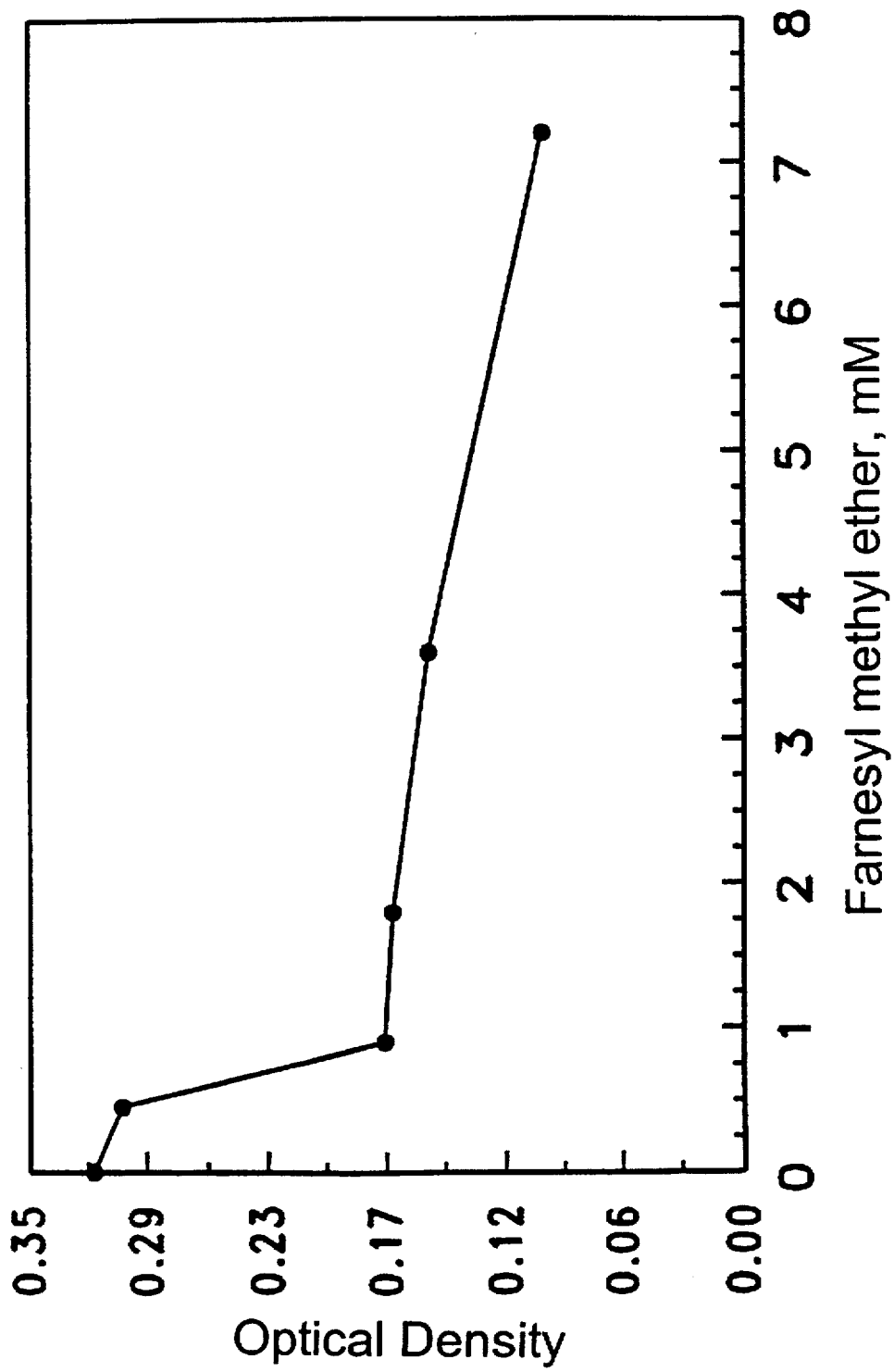
FIG. 3 shows the inhibition of bacterial growth resulting from the administration to *E. coli* of farnesyl methyl ether. The figure shows significant inhibition of bacterial growth.
Figure 4:
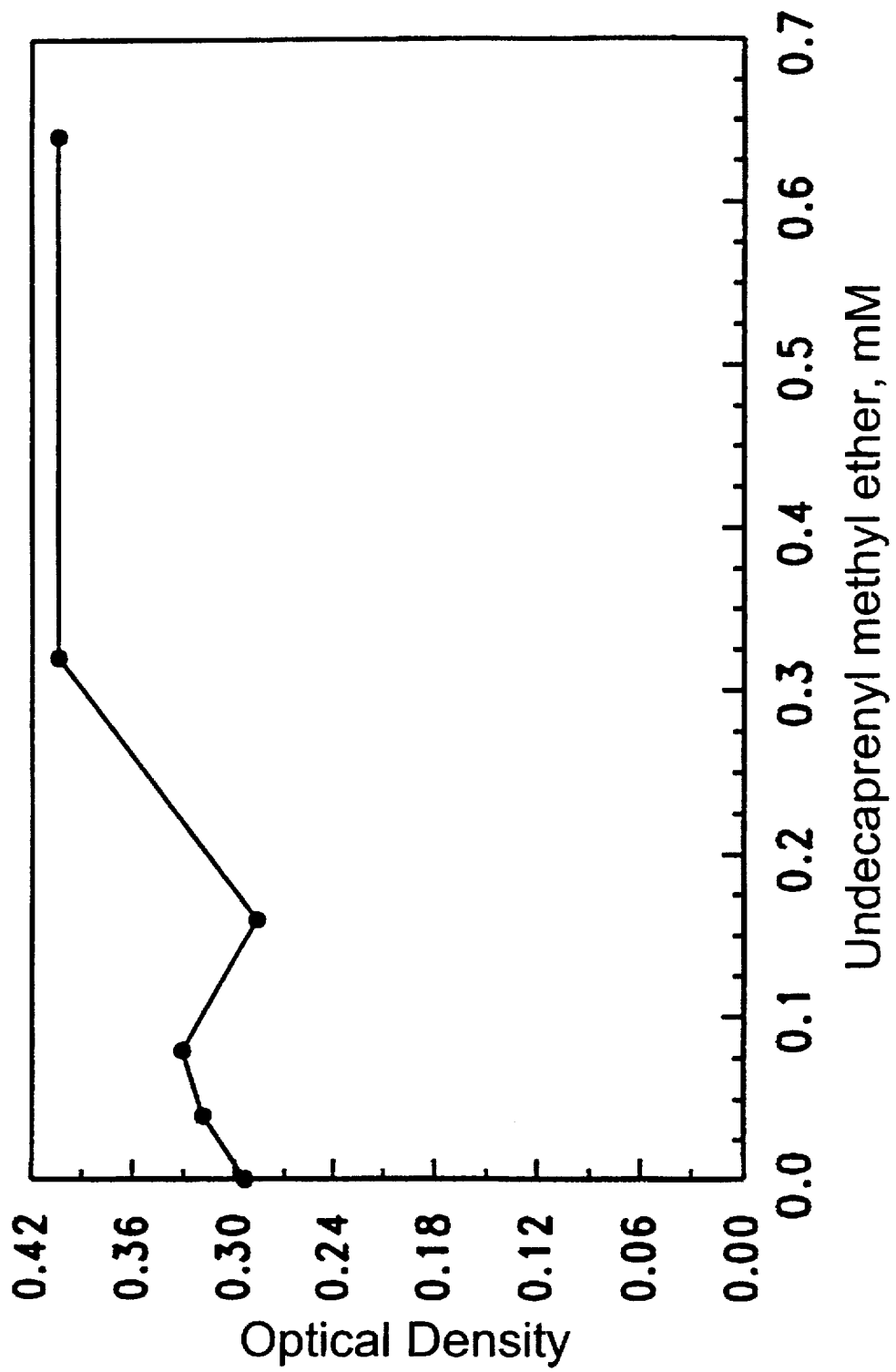
FIG. 4 shows significant inhibition of *E. coli* growth resulting from the administration to *E. coli* of bacitracin—a well-known antibiotic.
Figure 5:
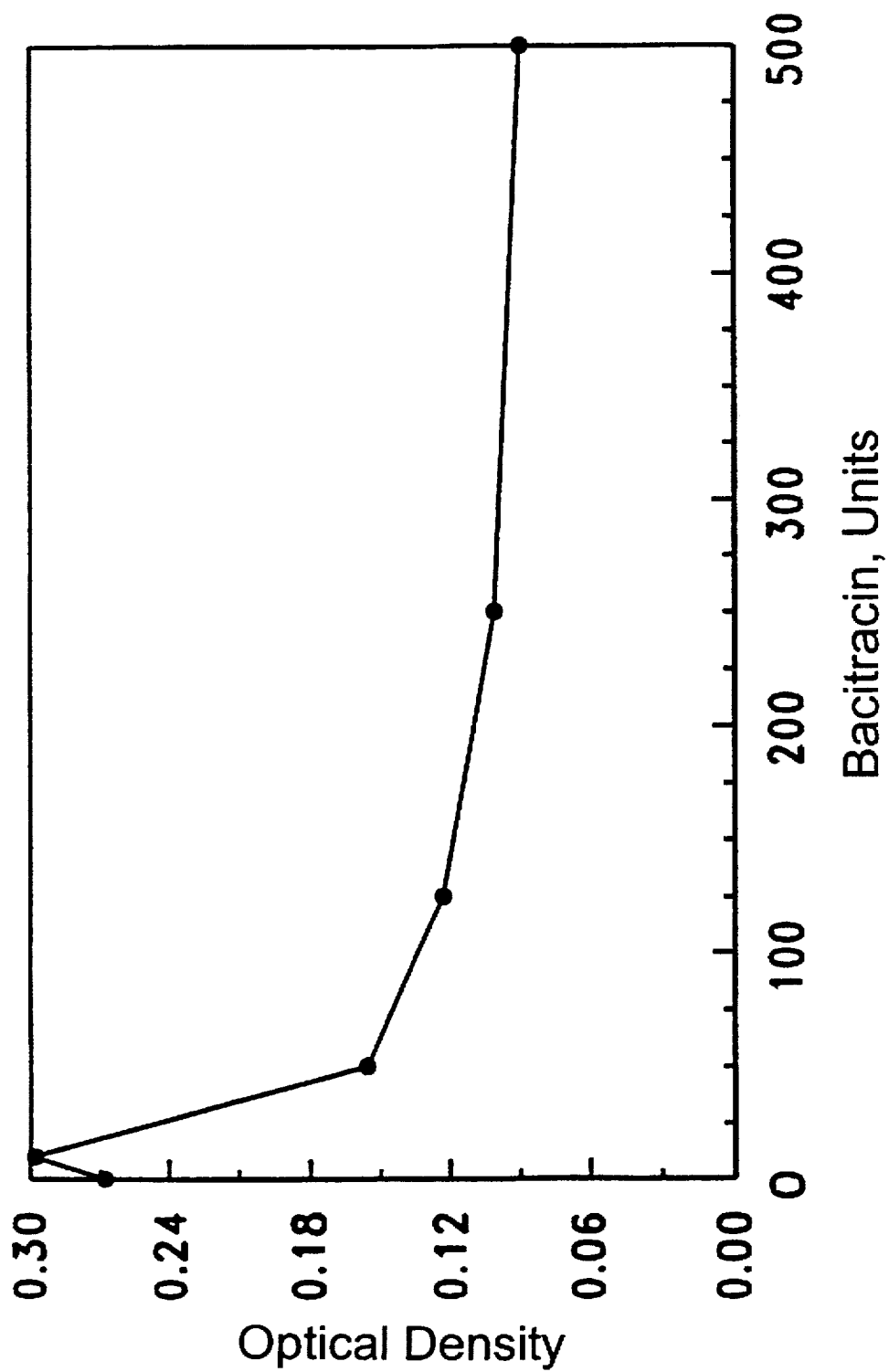
FIG. 5 shows the effect on *E. coli* growth resulting from the administration of undecaprenyl methyl ether.

The subject invention provides materials and methods useful in the inhibition of bacterial growth. As used herein, reference to "inhibition" of bacterial growth refers to a reduction or prevention of bacterial multiplication (bacteriostatic) as well as to actual killing of bacteria (bacteriocidal). The inhibition of bacterial growth achieved according to the subject invention is accomplished through the administration of compounds which interfere with a bacterial cell's ability to synthesize the cell wall. The inhibition of cell wall biosynthesis is accomplished according to the subject invention by interfering with the cell's supply of the $C_{55}$ isoprenoid lipid known as undecaprenyl phosphate ($C_{55}$-P). This lipid is a critical component of the metabolic pathway by which saccharides are transported across the plasma membrane into the periplasmic space for ultimate incorporation into the cell wall. The metabolic pathway for cell wall biosynthesis is depicted in FIG. 1.

In accordance with the subject invention, a bacterial cell's supply of $C_{55}$-P can be reduced by disrupting the enzymatic reaction which converts $C_{55}$OH to $C_{55}$-P. This conversion is facilitated through the activity of a kinase known as the undecaprenol kinase enzyme. According to the subject invention the ability of the undecaprenol enzyme to catalyze the reaction which produces $C_{55}$-P is decreased by administration of inhibitor compounds.

In a specific embodiment, the subject invention provides substrate mimics which can be, for example, lipid ethers which compete with $C_{55}$OH for the undecaprenol kinase enzyme thereby reducing the rate of conversion of $C_{55}$OH to $C_{55}$-P. Typically, the substrate mimics of the subject invention would not have a terminal hydroxyl group. Instead, an ether group or other group which cannot be enzymatically converted by the kinase is present on the substrate mimic. In a preferred embodiment, the ether is a methyl or ethyl ether, but other ethers could also be used. By disrupting the normal metabolism of $C_{55}$-P according to the subject invention it is possible to achieve a cessation or significant inhibition of cell wall synthesis. Consequently, bacterial growth is inhibited.

In a particularly preferred embodiment of the subject invention, the antibacterial compounds have carbon chains of less than $C_{55}$ thereby increasing the water solubility of these compounds. A person skilled in the art having the benefit of the instant disclosure can identify compounds which have carbon chains of sufficient length to disrupt the enzymatic activity of the undecaprenol kinase enzyme while maintaining a desired degree of water solubility. These compounds are preferably unsaturated to best mimic the native $C_{55}$OH molecule. However, the degree of unsaturation as well as the stereochemistry of the inhibitor compound can be modified so long as the ability to disrupt enzymatic activity is retained. It should also be noted that any negative aspects of low water solubility can be minimized or eliminated through various formulation modifications and/or appropriate selection of the mode of administration. For example, the water solubility of these lipid compounds can be enhanced through the use of cyclodextrins which enhance water solubility of the lipid compounds without hindering the bioavailability of those compounds. In another embodiment, the inhibitor compounds of the subject invention can be encapsulated within a liposome or other delivery vehicle. Liposome and cyctodextrin technologies, and other such technologies useful for enhancing water solubility, are well known and easily practiced by those skilled in the art and can be readily applied in conjunction with the teachings provided herein.

Thus, in a preferred embodiment, the subject invention pertains to the inhibition of the activity of the undecaprenol kinase enzyme. It has been determined that the undecaprenol kinase enzyme is an important enzyme for bacterial extracellular glycan biosynthesis. The enzyme produces the lipid carbohydrate carrier, undecaprenyl phosphate, which is required by bacteria for their survival. The inhibition of the undecaprenol kinase enzyme inhibits the synthesis of extracellular glycans and therefore, bacterial cell growth.

The compounds of the subject invention can be used to control a variety of pathogenic bacteria including, for example, *M. tuberculosis*, the cause of tuberculosis. Mycobacteria in general are difficult to kill because of their resistance to most common antibiotics and the prevalence of drug-resistant strains increases the danger of tuberculosis. This resistance has been attributed to an unusual cell wall structure and the low permeability of mycobacteria to most antibiotics. Some of the most effective antibiotics against *M. tuberculosis* are hydrophobic compounds, that are able to pass this hydrophobic barrier. The hydrophobic nature of the isoprenol ethers of the subject invention make these compounds particularly advantageous as inhibitors of this bacterium. Other bacteria which can be controlled include Staphylococcus pathogens as well as other bacterial pathogens. Also, the compounds of the subject invention can be used to disinfect surfaces such as laboratory workbenches.

The active compounds of the subject invention can be used, for example, in the form of injectable compositions, e.g. for intravenous administration, or for infusion solutions. Such solutions are preferably isotonic aqueous solutions or suspensions which can be prepared prior to use, e.g. from lyophilished preparations which contain the active ingredient alone or together with a carrier, e.g. mannitol. Pharmaceutical compositions for oral administration may be sterilized and can contain adjuvants, e.g., preservatives, stabilizers, wetting agents and/or emulsifiers, solubilisers, salts for regulating the osmotic pressure, resorption promoters and/or buffers. The pharmaceutical compositions of this invention which, if desired, may contain further useful pharmacological substances, e.g. other active ingredients, can contain about 0.1 to 100%, preferably about 1 to 100%, of active ingredient.

The compounds of the present invention can be presented for administration to humans and animals in unit dosage forms, such as sterile parenteral solutions or suspensions, containing suitable quantities of active compound. Unit dosage forms may also be as tablets, capsules, pills, powders, granules, oral solutions or suspensions, and water-in-oil emulsions containing suitable quantities of compounds.

For oral administration, either solid or fluid unit dosage forms can be prepared. For preparing solid composition such as tablets, the unit dosage is mixed with conventional ingredients such as talc, magnesium stearate dicalcum phosphate, magnesium aluminum silicate, calcium sulfate, starch, lactose, acacia, methylcellulose, and functional similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin together with an aromatic flavoring agent.

Suspensions can be prepared with an aqueous vehicle with the aid of a suspending agent such as acacia, tragacanth, metylcellulose and the like.

For parenteral administration fluid unit dosage forms are prepared utilizing the active compounds and a sterile vehicle. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the compositions can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same oral suspensional manner except that the compound is suspended in the vehicle instead of being dissolved. The compound can be sterilized by exposure to ethylene oxide before suspending in the sterile vehicle. Advantageously, a surfactant or wetting agent is included in the composition to facilitate uniform distribution of the compound.

The term "unit dosage form," as used in the specification, refers to physically discrete units suitable as unitary dosages for human subjects and animals, each unit containing a predetermined quantity of active material calculated to produce the desired therapeutic effect in association with the required pharmaceutical diluent, carrier or vehicle. The specification for the novel unit dosage forms of this invention are dictated by and directly dependent on (a) the unique characteristics of the active material and the particular effect to be achieved and (b) the limitations inherent in the art of compounding such an active material for use in human and animals, as disclosed in detail in this specification, these being features of the present invention. Examples of suitable unit dosage forms in accord with this invention are ampoules and vials, as well as tablets, capsules, pills, powder packets, wafers, granules, cachets, teaspoonfuls, tablespoonfuls and dropperfuls, segregated multiples of the foregoing, and other forms as herein described.

An effective quantity of the compound is employed in treatment. The dosage of the compound for treatment depends on many factors that are well known to those skilled in the art. They include, for example, the route of administration and the potency of the particular compound. A dosage schedule for humans of from about 500 to about 5000 mg of compound in a single dose, administered parenterally are effective for treating bacterial infections. When initial dosages at the lower end of the above range are employed, the mammal's progress can be monitored and dosages on subsequent days increased in the event that the patient or animal response is deemed by the attending physician or veterinarian to be absent or insufficient. The systemic toxicity of compounds of this invention can be carefully evaluated and subsequent dosages determined by evaluating the benefits of the drug in relationship to any such toxic manifestations.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycol such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The pharmaceutical compositions can be prepared by conventional dissolving or lyophilizing methods described textbooks of pharmacology.

The compounds described herein are useful antibiotic agents in animals. The term "animals" is intended to include inter alia mammals, such as mice, rats, rabbits, dogs, cats, cows, horses and primates including man. Also encompassed within the term animals are both fish and fowl. The term "fowl" is intended to include male or female birds of any kind, but is primarily intended to encompass poultry which are commercially raised for eggs or meat.

Following are examples which illustrate procedures for practicing the invention. These examples should not be construed as limiting. All percentages are by weight and all solvent mixture proportions are by volume unless otherwise noted.

EXAMPLE 1

Inhibition of Bacterial Growth

In one embodiment, the subject invention provides inhibitors of the undecaprenyl kinase enzyme. Specifically, ethers of isoprenyl alcohols were tested as inhibitors of bacterial growth. *E. coli* cells were grown for 18 hours on an appropriate growth medium in the presence of the various test compounds. Cells were then harvested and the amount of protein present was measured using an optical density determination. For example, farnesyl methyl ether was tested to determine its ability to inhibit bacterial growth. The results of inhibition studies showed clearly that the farnesol methyl ether was an effective inhibitor of the growth of *E. coli* at concentrations comparable to those found with bacitracin to inhibit bacterial growth. The parent alcohol, farnesol was ineffective in inhibiting bacterial growth over a similar concentration range. The results of these experiments ar shown in FIGS. 2–5.

The antibacterial use of other compounds which inhibit the ability of the undecaprenol kinase enzyme to convert $C_{55}OH$ to $C_{55}$-P are within the subject invention.

EXAMPLE 2

Formulation and Administration

The compounds of the subject invention are useful for various non-therapeutic and therapeutic purposes. It is apparent from the testing that the compounds of the invention are effective for controlling bacterial growth.

Therapeutic application of the compounds and compositions comprising them can be accomplished by any suitable therapeutic method and technique presently or prospectively known to those skilled in the art.

As would be appreciated by those skilled in the art, the dosage administration will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for inhibiting bacterial growth which comprises administering to said bacteria an effective amount of a compound which interferes with the enzymatic conversion of undecaprenol to undecaprenyl phosphate.

2. The method, according to claim 1, wherein said compound interferes with said enzymatic conversion by acting as a substrate mimic.

3. The method, according to claim 2, wherein said compound is a lipid compound having from about 10 to about 60 carbons.

4. The method, according to claim 1, wherein said compound is an ether.

5. The method, according to claim 3, wherein said compound is a methyl ether.

6. The method, according to claim 5, wherein said compound has between about 15 and about 35 carbons.

7. The method, according to claim 6, wherein said compound has about 15 carbons.

8. The method, according to claim 7, wherein said compound is farnesyl methyl ether.

9. The method, according to claim 1, wherein said method is used to treat a bacterial infection in a mammal.

10. The method, according to claim 9, wherein said mammal is a human.

* * * * *